(12) United States Patent
Zavala (10) Patent No.: US 9,549,714 B2
(45) Date of Patent: *Jan. 24, 2017

(54) ENDOMETRIAL SAMPLE COLLECTOR (71) Applicant: INNOVA-TECH, LLC, Miami, FL (US)

(72) Inventor: Carlos Fidel Miranda Zavala, Guayaquil (EC)

(73) Assignee: INNOVA-TECH, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/858,978

(22) Filed: Sep. 18, 2015

(65) Prior Publication Data

US 2016/0143631 A1    May 26, 2016

Related U.S. Application Data

(63) Continuation of application No. 14/318,138, filed on Jun. 27, 2014, now Pat. No. 9,144,420.

(30) Foreign Application Priority Data

Jun. 28, 2013   (EC) .............................. SP2013-12745

(51) Int. Cl.
*A61B 10/00*   (2006.01)
*A61B 10/02*   (2006.01)
(Continued)

(52) U.S. Cl.
CPC ....... *A61B 10/0045* (2013.01); *A61B 10/0291* (2013.01); *A61F 13/2034* (2013.01);
(Continued)

(58) Field of Classification Search
CPC ............ A61B 10/0291; A61B 10/0045; A61B 2010/0074
See application file for complete search history.

(56) References Cited

U.S. PATENT DOCUMENTS 3,850,160 A   11/1974   Denson
4,257,427 A    3/1981   Bucalo
(Continued)

FOREIGN PATENT DOCUMENTS

WO   WO 2012/118494    9/2012

OTHER PUBLICATIONS

International Search Report and Written Opinion mailed on Nov. 24, 2014 in PCT/US2014/004693.

*Primary Examiner* — Rene Towa
(74) *Attorney, Agent, or Firm* — Knobbe, Martens, Olson & Bear, LLP (57) ABSTRACT

A non-invasive endometrial sample collector has an outer body of absorbent material configured for insertion into a vaginal cavity of a patient such that a distal end of the body is positioned proximate a uterine cervix of the patient. The collector has an internal collection assembly disposed within the outer body of absorbent material. The internal collection assembly includes a funnel having an opening at the distal end of the outer body configured to face the uterine cervix when the outer body is positioned in the vaginal cavity, and a reservoir in fluid communication with the funnel. During a menstruation cycle of the patient when endometrial tissue cells are shed within menstrual fluid that passes through the uterine cervix, or during any type of normal or abnormal bleeding episode, at least a portion of said fluid is directed to the reservoir via the funnel under the force of gravity.

13 Claims, 5 Drawing Sheets

(51) Int. Cl.
*A61F 13/20* (2006.01)
*A61F 13/34* (2006.01)

(52) U.S. Cl.
CPC .......... *A61F 13/2042* (2013.01); *A61F 13/34* (2013.01); *A61B 2010/0074* (2013.01)

(56) References Cited

U.S. PATENT DOCUMENTS

| | | |
|---|---|---|
| 4,317,454 A | 3/1982 | Bucalo |
| 5,725,481 A | 3/1998 | Buck et al. |
| 5,810,745 A | 9/1998 | Chaffringeon |
| 5,823,954 A | 10/1998 | Chaffringeon |
| 5,830,199 A | 11/1998 | Chaffringeon |
| 2001/0047136 A1 | 11/2001 | Domanik et al. |
| 2003/0028123 A1 | 2/2003 | Pevoto |
| 2013/0172778 A1 | 7/2013 | Teschendorf |

FIG. 8

ENDOMETRIAL SAMPLE COLLECTOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation application of U.S. application Ser. No. 14/318,138 filed Jun. 27, 2014, now U.S. Pat. No. 9,144,420, which claims priority to Ecuadorean Patent Application No. SP2013-12745 filed on Jun. 28, 2013, the entire contents of which are hereby incorporated by reference and should be considered a part of this specification.

BACKGROUND

Field

The present application is directed to a system for collecting an endometrial tissue sample, and more particularly to a non-invasive endometrial sample collector.

Description of the Related Art

There are several existing procedures for obtaining samples of endometrial tissue. One such procedure involves the sampling of the endometrium with a small plastic device that is introduced in the uterine cavity and through the uterine cervix in order to obtain the tissue sample. This procedure is usually performed in a doctor's office, without anesthesia.

Another existing procedure for obtaining an endometrial tissue sample involves cervical dilation and curettage (D&C). The D&C procedure requires insertion of instruments (e.g., curette or sharp curettage, suction curettage, electric vacuum aspiration) in the uterine cavity and through the uterine cervix to remove endometrial tissue samples, such as by scraping and scooping the endometrial tissue sample. This procedure is performed in a hospital, under anesthesia. The procedure is often performed blindly by the doctor (e.g., without the use of any imaging technique such as ultrasound or hysteroscopy).

Still another existing procedure for obtaining an endometrial tissue sample involves a hysteroscopy. This procedure involves introducing an optical system (e.g., endoscope) within the uterine cavity and through the uterine cervix to directly observe the endometrium. The endoscope can have operative channels through which instruments (e.g., biopsy instruments, resectoscope) can be deployed to obtain a sample of the endometrial tissue under the visual guidance provided by the optical system. Such a procedure can be performed at a hospital or surgical centers, or a clinic, and can be performed under local anesthesia. Hysteroscopies are more expensive procedures (from the patient's and doctor's point of view) since they require expensive equipment and trained specialists.

All of the above described existing procedures for obtaining endometrial tissue samples have numerous disadvantages and potential risks to the patient, including: the risk of infection (e.g., due to the introduction of instruments into the vaginal cavity); the risk of perforating the endometrium and uterine wall (e.g., and possibly damage other organs, such as the intestines); severe bleeding (even in the absence of perforation of the endometrium); endometrial lesions by scarring, leading to infertility (i.e., Asherman's Syndrome); the risk of interrupting an existing but undiagnosed pregnancy; the risk of side effects from antibiotics or pain medication; the risks associated with anesthesia; pain and/or discomfort to the patient; interruption of sexual activity following the procedure; interruption of work and/or social activity for the patient following the procedure; and the risk of allergic reactions to drugs (e.g., antibiotics, analgesic, anesthesia, etc.), iodine (used for cleaning the uterine cervix and vagina during the procedure), latex (e.g., surgical gloves). Other drawbacks of existing procedures include the amount of time the procedures take, the elevated cost of the procedures and the complications they cause in the patient's lives (e.g., anxiety, interruption of work, family interactions and sexual activity).

SUMMARY

Accordingly, there is a need for an improved system and method for obtaining an endometrial tissue sample that does not suffer from the drawbacks associated with existing procedures, such as those described above.

In accordance with an aspect of the invention, an endometrial sample collector is provided. The collector comprises an outer body of absorbent material configured for insertion into a vaginal cavity of a patient such that a distal end of the body is positioned proximate a uterine cervix of the patient. The collector also comprises an internal collection assembly disposed within the outer body of absorbent material. The internal collection assembly comprises a funnel having an opening at the distal end of the outer body configured to face the uterine cervix when the outer body is positioned in the vaginal cavity, and a reservoir in fluid communication with the funnel. During a menstruation cycle of the patient when endometrial tissue cells are shed within menstrual fluid that passes through the uterine cervix, at least a portion of said menstrual fluid is directed to the reservoir via the funnel under the force of gravity.

In accordance with an aspect of the invention, an endometrial sample collector is provided. The collector comprises an outer body of absorbent material configured for insertion into a vaginal cavity of a patient such that a distal end of the body is positioned proximate a uterine cervix of the patient. The collector also comprises an internal collection assembly disposed within the outer body of absorbent material. The internal collection assembly comprises a funnel having an opening at the distal end of the outer body configured to face the uterine cervix when the outer body is positioned in the vaginal cavity, a conduit in fluid communication with the funnel, and a reservoir in fluid communication with the conduit. During a menstruation cycle of the patient when endometrial tissue cells are shed within menstrual fluid that passes through the uterine cervix, at least a portion of said menstrual fluid is directed to the reservoir via the funnel and the conduit under the force of gravity.

In accordance with an aspect of the invention, a method for passively collecting an endometrial tissue sample is provided. The method comprises inserting a sample collector into a vaginal cavity of a patient so that a distal end of the collector is positioned proximate a uterine cervix of the patient. The method also comprises collecting an endometrial sample in the sample collector during a menstrual cycle of the patient or during any type of normal or abnormal bleeding solely under the force of gravity. The method also comprises sending the sample collector with the collected sample to a laboratory for evaluation.

DETAILED DESCRIPTION

Figure 1:
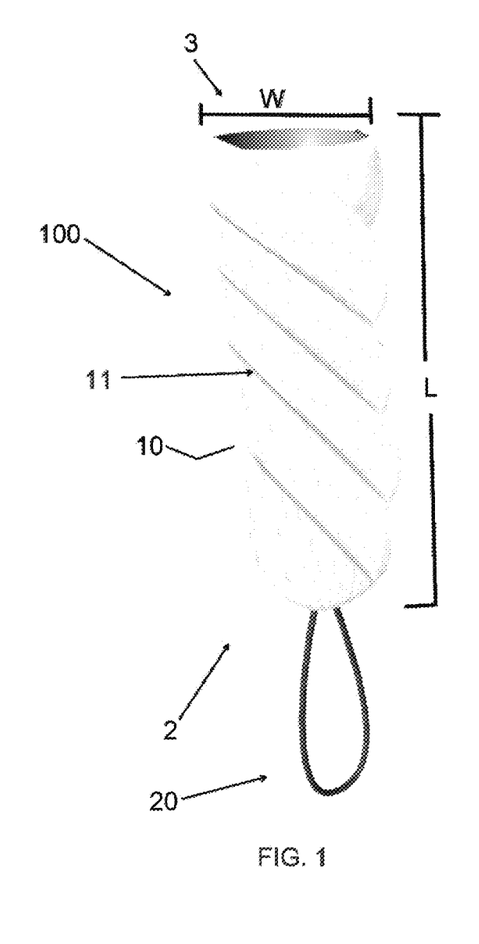
FIG. 1 is a schematic perspective top view of an endometrial sample collector.

FIGS. 1-4 show and endometrial sample collector 100 that extends between a proximal end 2 and a distal end 3 and includes and outer body 10 and an internal collection assembly 50. The outer body 10 is of an absorbent material (e.g., cotton, rayon, sponge material, absorbent polymer), such as the material used in typical tampons, and has absorption channels 11 through which fluid passes toward the internal collection assembly 50. The outer body 10 of absorbent material advantageously facilitates patient comfort during collection of an endometrial sample in the manner discussed further below. The sample collector 100 can have a thread or cord 20 attached to it to aid in the removal of the collector 100. As shown in FIG. 1, the thread or cord 20 is in the form of a loop. However, the thread or cord 20 can optionally be a single string that extends to a free end (e.g., not a loop).

The endometrial sample collector 100 has a length L between the proximal end 2 to the distal end 3 of between about 4 cm and about 6 cm, and has a width W of between about 1 cm and about 3 cm. However, the endometrial sample collector can have other suitable dimensions.

Figures 2, 3:
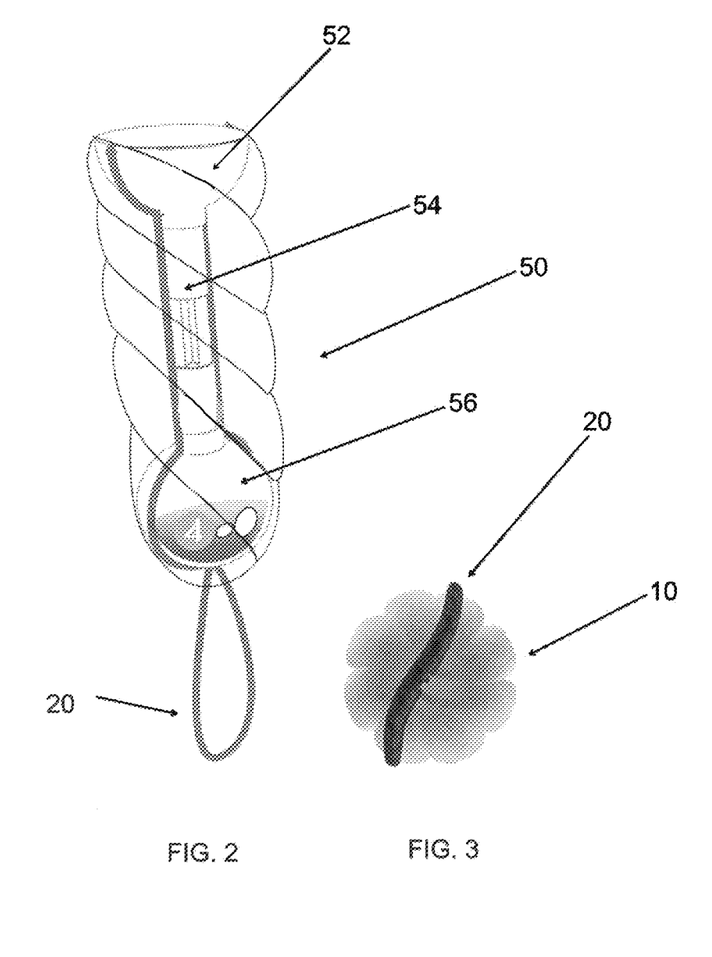
FIG. 2 is a schematic perspective top view of the endometrial sample collector of FIG. 1, showing internal components of the collector in phantom.
FIG. 3 is a schematic bottom view of the endometrial sample collector of FIG. 1.
Figure 4:
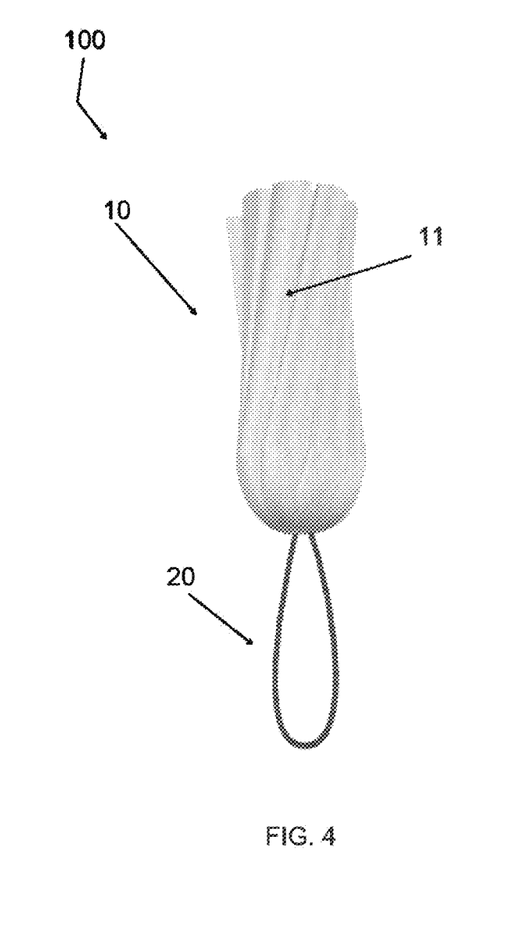
FIG. 4 is a schematic front view of the endometrial sample collector.

The inner collection assembly 50 can be wrapped by the outer body 10. The collection assembly has a cup or funnel 52 with an open end at the distal end 3 of the collector 100 that receives the sample therein. The funnel 52 is in fluid communication with a conduit 54, which is itself in communication with a reservoir 56, such that the conduit 54 is interposed between the funnel 52 and the reservoir 56. The reservoir 56 can be at least partially filled with a fluid 4 that preserves the endometrial sample once received. The funnel 52, conduit 54 and reservoir 56 can be separate components that are coupled together to form the collection assembly 50. Optionally, the funnel 52, conduit 54 and reservoir 56 can be made as a single monolithic piece (e.g., via an injection molding process). In other variations, the funnel can be augmented to have, or can be replaced with, a mesh or screen or permeable layer (e.g., foam layer) through which the sample fluid can pass to the reservoir 56. The funnel 52, conduit 54 and reservoir 56 can be made of a bio-compatible material, such as a plastic material, or other suitable material. The conduit 54 can optionally be excluded and the funnel 52 be in fluid communication with the reservoir 56.

As discussed above, the fluid 4 in the reservoir 56 facilitates preservation of the collected endometrial sample. In one embodiment, the fluid 4 can be sterile saline. In another embodiment, the fluid 4 can be a solution made from a 1 L amount of distilled water in combination with the following composition: 0.9 gm/L Sodium Thioglycollate, 10.0 gm/L Sodium Glycerophosphate, 0.1 gm/L Calcium Chloride, and 3.0 gm/L Agar. The solution has a pH of 7.4±0.2. In some embodiments, the composition can optionally include 0.002 gm/L of methylene blue.

Figure 5:
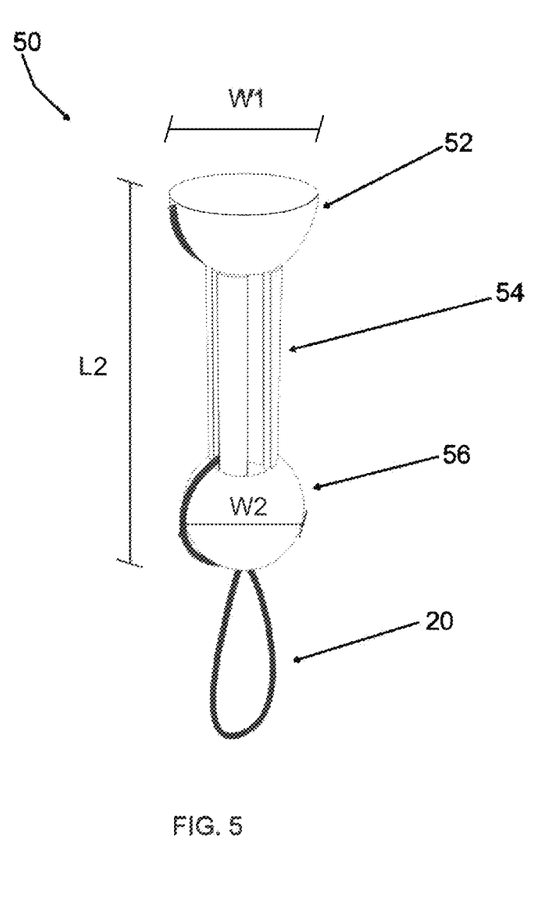
FIG. 5 is a schematic perspective top view of one embodiment of a collection assembly of the endometrial sample collector.

As shown in FIG. 5, the collection assembly 50 can have a length L2 that is substantially equal to the length L of the collector 100. In one embodiment, the length L2 is about 6 cm. The funnel 52 has a width W1 (e.g., a diameter), and the reservoir 56 has a width W2, with the conduit 54 having a width smaller than the widths W1, W2 of the funnel 52 and reservoir 56. Optionally, the width of the conduit 54 can be generally equal to the widths W1, W2 of the funnel 52 and reservoir 56. The width W1 of the funnel 52 can optionally be substantially equal to the width W2 of the reservoir 56. Optionally, the widths W1, W2 (e.g., diameters) of the funnel 52 and reservoir 56 can be about 2 cm. As shown in FIG. 5, the reservoir 56 has a generally spherical shape. However, the reservoir 56 can have other suitable shapes (e.g., oval).

FIGS. 6A-6D show various embodiments of the collection assembly 50, in which the funnel 52 and reservoir 56 are the same, but where the conduit 54 is different for each embodiment.

Figure 6A:
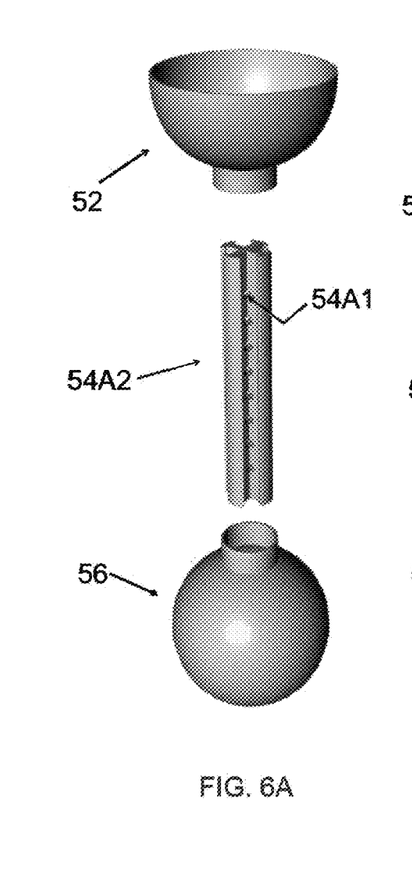
FIG. 6A is a schematic perspective top view of one embodiment of a collection assembly of the endometrial sample collector.
Figure 7A:
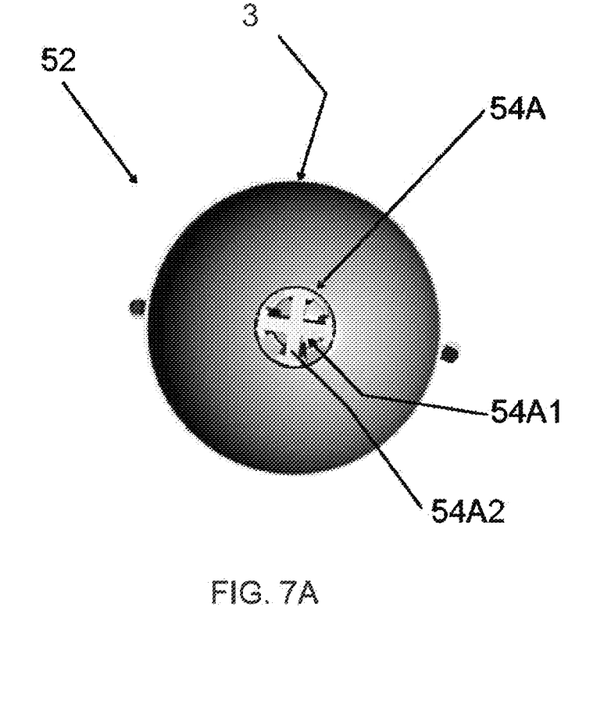
FIG. 7A is a schematic top view of the collection assembly of FIG. 6A.

In FIG. 6A, the conduit 54A has a cross-shaped cross-section (see FIG. 7A) that defines channels 54A2 between adjacent fins 54A2 of the conduit 54A. The channels 54A2 can extend along the length of the conduit 54A and can receive fluid axially from the funnel 52 as well as radially through the outer body 10 of absorbent material. The channels 54A2 can direct the sample fluid to the reservoir 56.

Figure 6B:
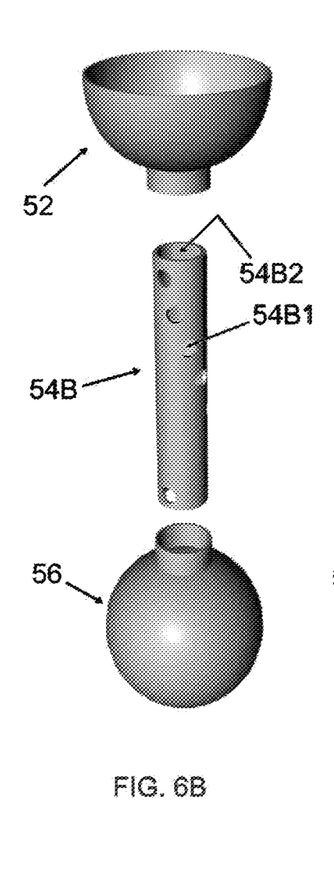
FIG. 6B is a schematic perspective top view of one embodiment of a collection assembly of the endometrial sample collector.

In FIG. 6B, the conduit 54B has a plurality of openings 54B1 distributed on a surface of the conduit 54B (e.g., in spiral form) that are in fluid communication with an inner flow channel 54B2 of the conduit 54B. Fluid can pass axially through the flow channel 54B2 from the funnel 52 to the reservoir 56 (see FIG. 7B). Fluid can also pass transversely from the outer body 10 of absorbent material, through the openings 54B1 and into the flow channel 54B2, which then directs the fluid to the reservoir 56.

Figures 6C, 6D:
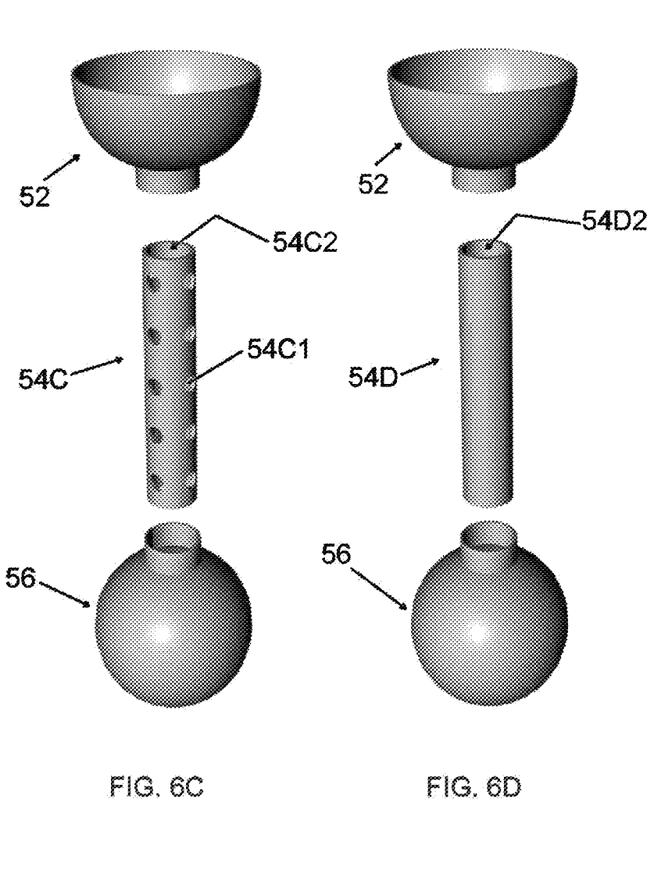
FIG. 6C is a schematic perspective top view of one embodiment of a collection assembly of the endometrial sample collector.
FIG. 6D is a schematic perspective top view of one embodiment of a collection assembly of the endometrial sample collector.

In FIG. 6C, the conduit 54C has a plurality of openings 54C1 distributed on a surface of the conduit 54C (e.g., in linear form) that are in fluid communication with an inner flow channel 54C2 of the conduit 54C. Fluid can pass axially through the flow channel 54C2 from the funnel 52 to the reservoir 56 (see FIG. 7B). Fluid can also pass transversely from the outer body 10 of absorbent material, through the openings 54C1 and into the flow channel 54C2, which then directs the fluid to the reservoir 56.

Figure 7B:
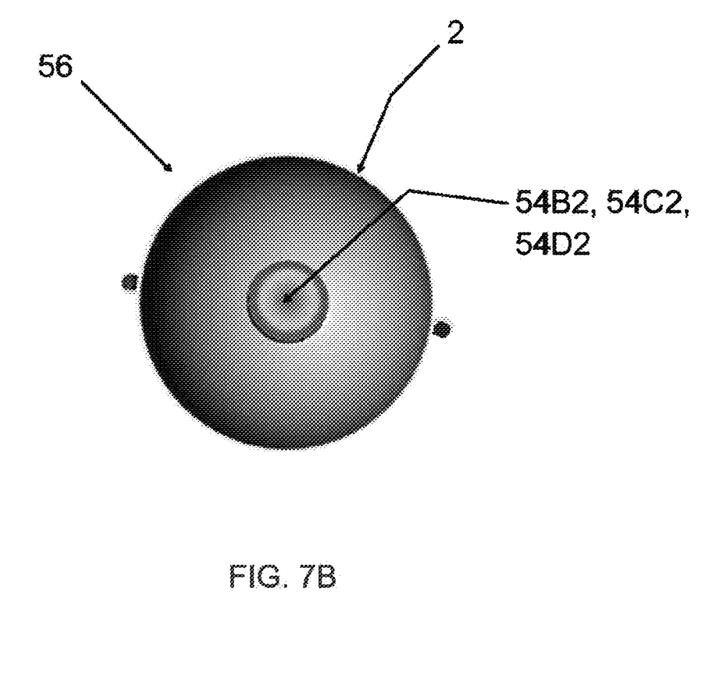
FIG. 7B is a schematic top view of the collection assembly of FIGS. 6B, 6C and 6D.

In FIG. 6D, the conduit 54D is a tube that without any openings on its outer surface and has an internal flow channel 54D2 that directs fluid from the funnel 52 to the reservoir 56, as shown in FIG. 7B.

Figure 8:
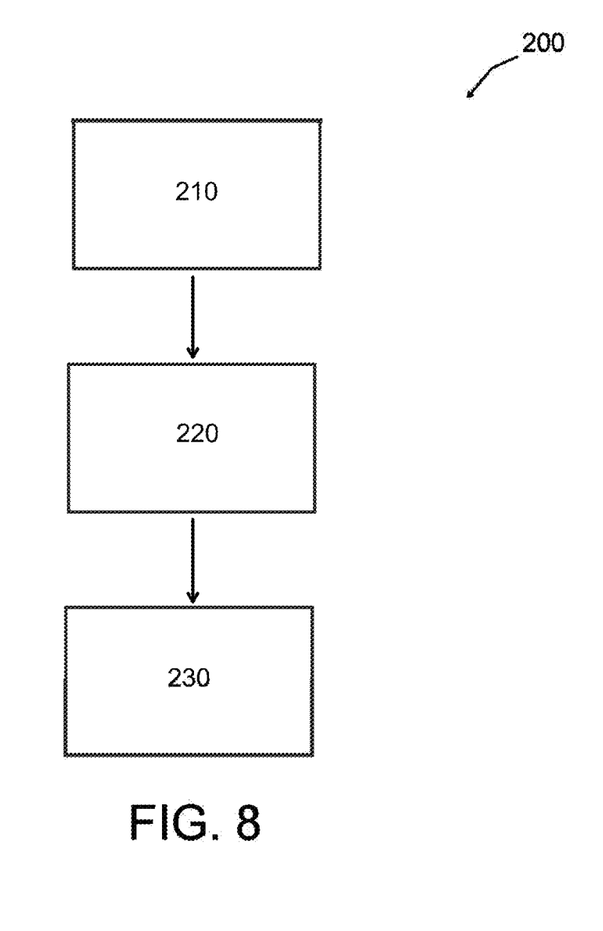
FIG. 8 is a block diagram illustrating a method of collecting an endometrial tissue sample.

FIG. 8 is a block diagram illustrating a method 200 of collecting an endometrial tissue sample using the sample collector 100. The sample collector 200 is first inserted 210

(e.g., by the patient) into the vaginal cavity, in a similar manner as a tampon, so that the distal end 3 of the collector is proximate the uterine cervix and so that the funnel 52 faces the uterine cervix. Optionally, the distal end 3 is placed in contact with the uterine cervix. During menstruation, menstrual fluid, which will include endometrial tissue that is shed during the menstrual cycle and passes through the uterine cervix, is collected 220 by the collector 100 in the manner discussed above. For example, menstrual fluid can be collected in the funnel 52 and directed via the conduit 54A, 54B, 54C, 54D to the reservoir 56, where the endometrial cells in the sample can be preserved in the preservation liquid 4. Additionally, menstrual fluid absorbed by the outer body 10 of absorbent material can be directed transversely through channels (e.g., 54A1) or openings (e.g., 54B1, 54C1) in a surface of the conduit 54A, 54B, 54C, which can then also be directed to the reservoir 56. Advantageously, the endometrial sample collector 100 passively collects the endometrial tissue sample using gravity and without the use of an external actuation force (e.g., without an aspiration or vacuum force, without a mechanical force such as scraping, etc.). Once the sample has been collected, the collector 100 can be can packaged in a container (e.g., plastic receptacle) and be sent 230 to a laboratory for evaluation. For example, the sample collector 100 can include user instructions directing the user on how to collect the sample, and how to package the sample for shipping to the laboratory, and optionally instructions on where to ship the collected sample.

Advantageously, the endometrial sample collector 100 and its use allows the patient to collect the sample without having to visit a doctor's office, clinic or hospital, and therefore without disruption to their normal daily activities. Additionally, the use of the collector 100 is non-invasive and does note expose the patient to the potential risks noted above with existing procedures (e.g., risk of infection, risk of perforation of the endometrium, pain and discomfort, bleeding, allergic reaction to medication, risks associated with anesthesia). Further, the sample collector 100 is as easy to use for patients as existing tampons. Additionally, the sample collector 100 can be used in patients with intact hymens (e.g., virgin women), patients that refuse gynecological exams or who live in remote areas far away from healthcare facilities, or patients who have problems adopting the correct gynecological position due to problems in their pelvic articulations, which is often the case following menopause. Further, the sample collector 100 allows the collection of endometrial tissue samples at much lower cost than existing procedures because, for example, doctor's fees (e.g., gynecologist, anesthesiologist), hospital fees, and disposable instruments and devices are avoided.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An endometrial sample collector, comprising:
    a body of absorbent material configured for insertion into a vaginal cavity of a female such that a distal end of the body is positioned proximate a uterine cervix of the female; and
    a collection assembly disposed within the body of absorbent material, the internal collection assembly comprising
    a funnel extending between an open first end and an open second end, the open first end having a larger circumference than the open second end, the open first end disposed proximate the distal end of the body and configured to face the uterine cervix when the body is positioned in the vaginal cavity,
    a conduit extending between a proximalmost end and an opposite distalmost end, the proximal most first end of the conduit attached to the second end of the funnel, and
    a reservoir attached to the distalmost second end of the conduit,
    wherein the funnel is configured to capture an endometrial sample comprising at least a portion of a menstrual fluid and endometrial tissue cells shed through the uterine cervix during the menstruation cycle of the female under the force of gravity and to direct said endometrial sample to the reservoir via the conduit, the reservoir configured to receive and hold said endometrial sample;
    wherein the conduit has a length greater than a length of the funnel and a length of the reservoir.

2. The endometrial sample collector of claim 1, wherein the conduit comprises a cross-shaped transverse cross-section that defines one or more channels between adjacent fins along a length of the conduit, and wherein said channels receive said least a portion of the menstrual fluid axially from the funnel, and wherein said one or more channels receive at least another portion of the menstrual fluid transversely via the body of absorbent material, the one or more channels configured to direct said axial and transverse fluid flows to the reservoir.

3. The endometrial sample collector of claim 1, wherein the reservoir further comprises a preservation fluid configured to preserve endometrial tissue cells.

4. The endometrial sample collector of claim 1, further comprising a thread or cord at a proximal end of the body for removal of the collector.

5. The endometrial sample collector of claim 1, wherein the body of absorbent material comprises one or more absorption channels.

6. The endometrial sample collector of claim 1, wherein the collection assembly has a length substantially the same as a length of the body.

7. An endometrial sample collector, comprising:
    a collection assembly configured for insertion into a vaginal cavity of a female, comprising
    a funnel extending between an open first end and an open second end, the open first end having a larger circumference than the open second end, the open first end configured to be disposed proximate to and configured to face the uterine cervix when the collection assembly is positioned in the vaginal cavity,
    a conduit extending between a proximalmost end and an opposite distalmost end, the proximalmost end of the conduit attached to the second end of the funnel, and
    a reservoir attached to the distalmost end of the conduit,
    wherein the funnel is configured to capture an endometrial sample comprising at least a portion of a menstrual fluid and endometrial tissue cells shed through the uterine cervix during the menstruation cycle of the female under the force of gravity and to direct said endometrial sample to the reservoir via the conduit, the reservoir configured to receive and hold said endometrial sample,
    wherein the conduit has a length greater than a length of the funnel and a length of the reservoir.

8. The endometrial sample collector of claim 7, wherein the reservoir further comprises a preservation fluid configured to preserve endometrial tissue cells.

9. The endometrial sample collector of claim 7, further comprising a body of absorbent material that surrounds the collection assembly, the body configured for insertion into the vaginal cavity of the female such that a distal end of the body is positioned proximate the uterine cervix of the female, said open first end of the funnel being proximate the distal end of the body.

10. The endometrial sample collector of claim 9, wherein the conduit comprises a cross-shaped transverse cross-section that defines one or more channels between adjacent fins along a length of the conduit, and wherein said channels receive said least a portion of the menstrual fluid axially from the funnel, and wherein said one or more channels receive at least another portion of the menstrual fluid transversely via the body of absorbent material, the one or more channels configured to direct said axial and transverse fluid flows to the reservoir.

11. The endometrial sample collector of claim 9, further comprising a thread or cord at a proximal end of the body for removal of the collector.

12. The endometrial sample collector of claim 9, wherein the body of absorbent material comprises one or more absorption channels.

13. The endometrial sample collector of claim 9, wherein the collection assembly has a length substantially the same as a length of the body.

* * * * *

UNITED STATES PATENT AND TRADEMARK OFFICE
CERTIFICATE OF CORRECTION

PATENT NO. : 9,549,714 B2  
APPLICATION NO. : 14/858978  
DATED : January 24, 2017  
INVENTOR(S) : Carlos Fidel Miranda Zavala Page 1 of 1

It is certified that error appears in the above-identified patent and that said Letters Patent is hereby corrected as shown below:

In the Claims

In Column 7 at Line 53, In Claim 1, change "proximal most first" to --proximalmost--.

In Column 7 at Line 56, In Claim 1, after "distalmost" delete "second".

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*